(12) United States Patent
Aguilar et al.

(10) Patent No.: US 8,265,743 B2
(45) Date of Patent: *Sep. 11, 2012

(54) FIXATION-LOCKED MEASUREMENT OF BRAIN RESPONSES TO STIMULI

(75) Inventors: Mario Aguilar, Jacksonville, AL (US);
Aaron Hawkins, Raleigh, NC (US);
Patrick Connolly, Durham, NC (US);
Ming Qian, Cary, NC (US)

(73) Assignee: Teledyne Scientific & Imaging, LLC, Thousand Oaks, CA (US)

( * ) Notice: Subject to any disclaimer, the term of this patent is extended or adjusted under 35 U.S.C. 154(b) by 443 days.

This patent is subject to a terminal disclaimer.

(21) Appl. No.: 12/645,663

(22) Filed: Dec. 23, 2009

(65) Prior Publication Data

US 2010/0100001 A1    Apr. 22, 2010

Related U.S. Application Data

(63) Continuation-in-part of application No. 11/965,325, filed on Dec. 27, 2007, and a continuation-in-part of application No. 12/356,681, filed on Jan. 21, 2009.

(51) Int. Cl.
*A61B 5/04* (2006.01)

(52) U.S. Cl. ...................................... 600/544

(58) Field of Classification Search .................. 600/544, 600/545
See application file for complete search history.

(56) References Cited

U.S. PATENT DOCUMENTS

| | | |
|---|---|---|
| 4,034,401 A | 7/1977 | Mann |
| 4,287,809 A | 9/1981 | Egli |
| 4,753,246 A | 6/1988 | Freeman |
| 5,231,674 A | 7/1993 | Cleveland |
| 5,513,649 A | 5/1996 | Gevins |
| 5,583,795 A | 12/1996 | Smyth |
| 5,617,872 A | 4/1997 | Scinto |
| 5,632,282 A | 5/1997 | Hay |
| 5,649,061 A | 7/1997 | Smyth |
| 5,797,853 A | 8/1998 | Musha |
| 5,846,208 A | 12/1998 | Pichimayr |
| 6,090,051 A | 7/2000 | Marshall |
| 6,092,058 A | 7/2000 | Smyth |
| 6,102,870 A | 8/2000 | Edwards |
| 6,230,049 B1 | 5/2001 | Fischell |
| 6,434,419 B1 | 8/2002 | Gevins |
| 6,572,562 B2 | 6/2003 | Marshall |
| 6,931,274 B2 | 8/2005 | Williams |
| 7,202,809 B1 | 4/2007 | Schade |
| 7,231,245 B2 | 6/2007 | Greenwald |
| 7,257,439 B2 | 8/2007 | Llinas |

(Continued)

OTHER PUBLICATIONS

Daimoto et al. "Effects of a Dual-Task Tracking on Eye Fixation Related Potentials (EFRP)" Human-Computer Interaction, Part III, HCII 2007, LNCS 4552, pp. 599-604.*

(Continued)

*Primary Examiner* — Navin Natnithithadha
*Assistant Examiner* — Etsub Berhanu
(74) *Attorney, Agent, or Firm* — Eric A. Gifford

(57) ABSTRACT

Fixation-locked measurement of brain activity generates time-coded cues indicative of whether an operator exhibited a significant cognitive response to task-relevant stimuli. The free-viewing environment is one in which the presentation of stimuli is natural to the task encompassing both pre- and post-fixation stimuli and the operator is allowed to move his or her eyes naturally to perform the task.

27 Claims, 12 Drawing Sheets

U.S. PATENT DOCUMENTS

| | | | |
|---|---|---|---|
| 7,344,251 | B2 | 3/2008 | Marshall |
| 7,438,418 | B2 | 10/2008 | Marshall |
| 2002/0099305 | A1 | 7/2002 | Fukushima |
| 2006/0189852 | A1* | 8/2006 | Greenwald et al. ............ 600/300 |
| 2007/0185697 | A1 | 8/2007 | Tan |
| 2007/0236488 | A1 | 10/2007 | Mathan |
| 2008/0188777 | A1 | 8/2008 | Bedziouk |

OTHER PUBLICATIONS

Adam D. Gerson, Cortically coupled computer vision for rapid image serach, IEEE Trans on Neural Systems and Rehabilitation Engineering, vol. 14, No. 2, pp. 174-179, Jun. 2006.

Simon Thorpe, Speed of processing in the human visual system, Nature, vol. 381, Jun. 6, 1006, pp. 520-522.

Lawrence M. Ward, Synchronous neural oscillations and cognitive processes, Trends in Cognitive Science, vol. 7, No. 12, Dec. 2003, pp. 553-559.

Canan Basar-Eroglu, P300-response: possible psychophysiological correlates in delta and theta frequency channels, A Review, International Journal of Psychophysiology 13, (1992).

W.Klimesh, Induced alpha band power changes in the human EEG and attention, Neuroscience Letters 244, (1998), pp. 73-76.

Eric Granholm, Pupillometric measures of cognitive and emotional processes, Internatinal Journal of Psychophysiology 42 (2004), pp. 1-6.

Lucas C. Parra, Recipes for the linear analysis of EEG, NeuroImage 28 (2005) pp. 326-341.

Marios G. Philiastides, Neural representation of task difficulty and decision making during perceptual categorization: a timing diagram, The Journal of Neuroscience, Aug. 30.

Lucas C. Parra, Response error correction—a demonstration of improved human machine performance using real-time EEG monitoring, IEEE Transactions on Neural Systems and Rehabilitation Engineering, vol. XX, No. Y, Month 2003.

German Gomez-Herrero, Automatic removal of ocular artifacts in the EEG without an EOG reference channel, Tampere University of Technology, Finland, 2006.

Olaf Dimingen, Long reading regressions are accompanied by a P600-like brain potential, Evidence from simultaneous recordings of eye movements and ERPs Department of Psychology, University of Pottsdam, Germany.

Olaf Dimingen, Measuring ERP effects of word predictability during left-to-right reading, Department of Psychology, University of Pottsdam, Germany.

Lucas C. Parra, Single trial detection in EEG and MEG; keeping it linear, Neurocomputing 52-54 (2003) pp. 177-183.

\* cited by examiner

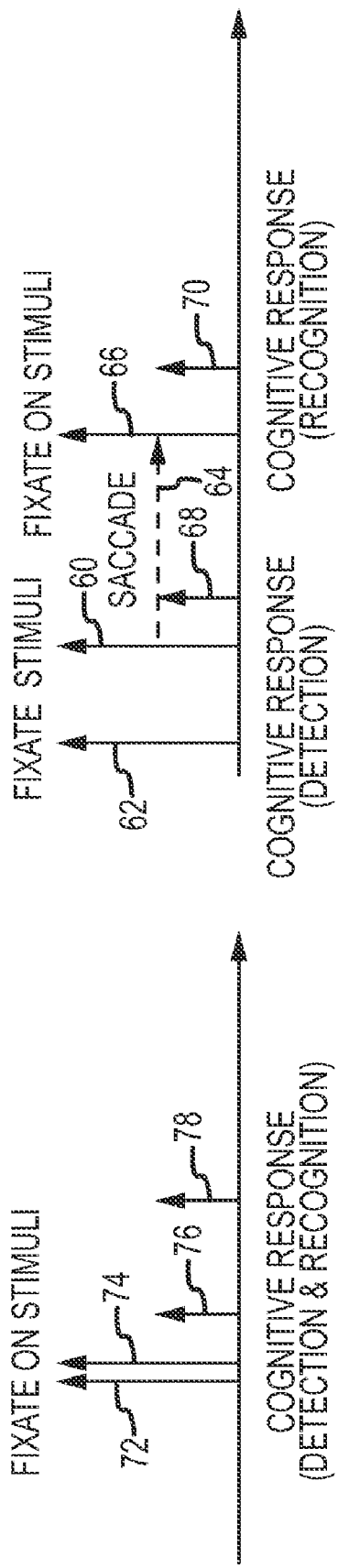

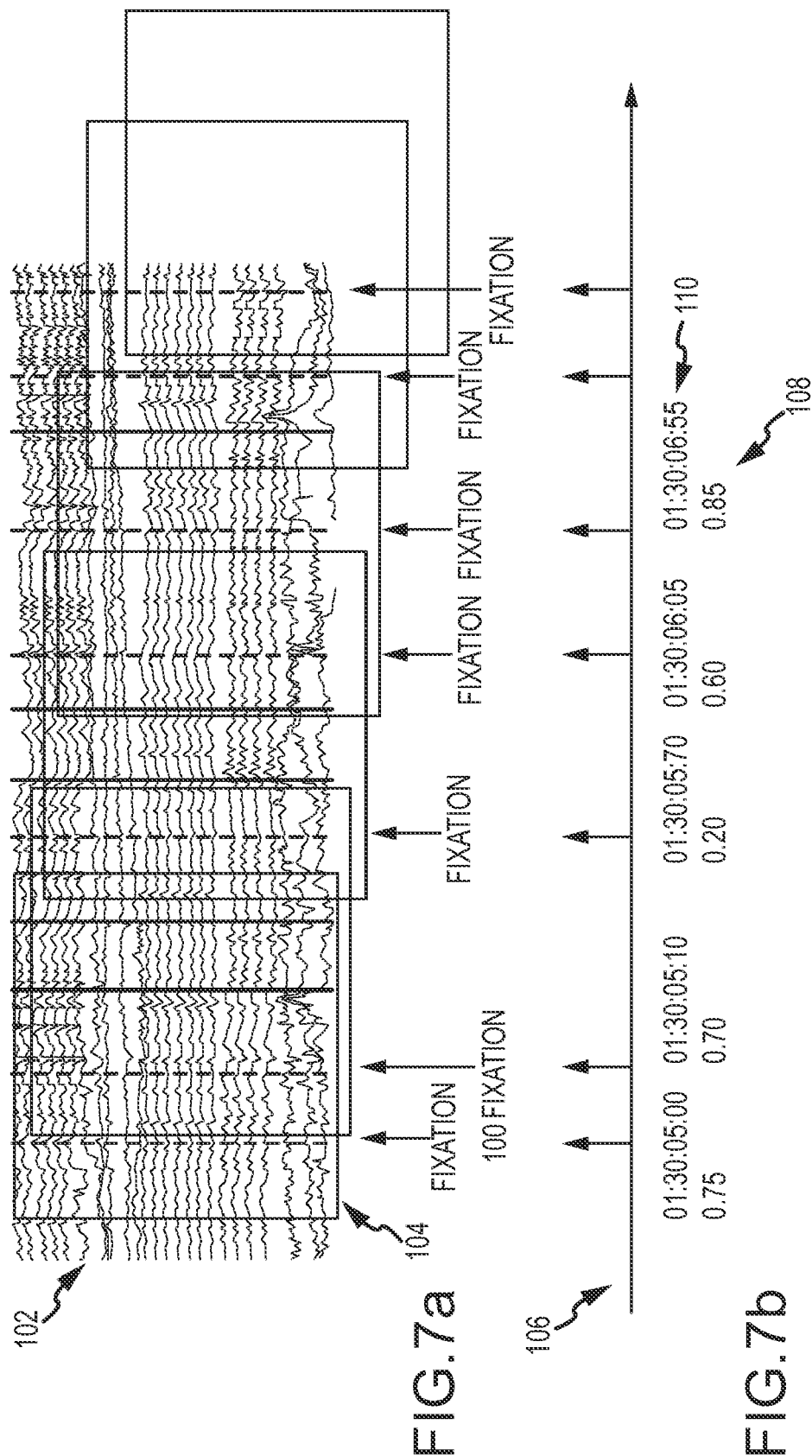

FIXATION-LOCKED MEASUREMENT OF BRAIN RESPONSES TO STIMULI

CROSS-REFERENCE TO RELATED APPLICATIONS

This application claims benefit of priority under 35 U.S.C. 120 as a continuation-in-part of co-pending U.S. Utility Applications No. 11/965,325 entitled "Coupling Human Neural Response with Computer Pattern Analysis for Single-Event Detection of Significant Brain Responses for Task-Relevant Stimuli" and filed on Dec. 27, 2007 and Ser. No. 12/356,681 entitled "Coordinating System Responses Based on an Operator's Cognitive Response to a Relevant Stimulus and to the Position of the Stimulus in the Operator's Field of View" and filed on Jan. 21, 2009, the entire contents of which are incorporated by reference.

GOVERNMENT RIGHTS

This invention was made with Government support under contract NBCHC080031 awarded to Teledyne Scientific & Imaging, LLC by the Department of the Interior (DOI) National Business Center (NBC) on behalf of the Defense Advanced Research Projects Agency (DARPA) Defense Sciences Office (DSO). The Government has certain rights in this invention.

BACKGROUND OF THE INVENTION

1. Field of the Invention

This invention relates to the measurement of brain responses to stimuli in which the presentation of the stimuli is natural to the task and an operator is allowed to move his or her eyes freely in performance of the task.

2. Description of the Related Art

A person's cognitive responses associated with task-relevant brain activity (both conscious and unconscious) may be monitored to study human neurophysiology, perform clinical diagnosis and to detect significant responses to task-relevant or environmental stimuli. In the latter, the detection of such a response may be fed back or used in some manner in conjunction with the task or environment. For example, the response could be used in a classification system to detect and classify visual, auditory or information stimuli, a warning system to detect potential threats, a lie detector system etc. The detection of a significant cognitive response generates a cue that the operator's neurophysiology has responded in a significant way.

Various techniques for monitoring neurophysiological responses as a correlate to cognitive responses include electroencephalography (EEG), pupil dilation and blood flow or oxygenation, each of which has been correlated to changes in neurophysiology. EEG signals represent the aggregate activity of millions of neurons on the cortex and have high time-resolution (capable of detecting changes in electrical activity in the brain on a millisecond-level). Evidence suggests significant amplitude differences between trial-averaged EEG responses triggered by task-relevant stimuli versus trial-averaged EEG responses triggered by neutral stimuli. The benefit of integrating EEG responses across multiple trials is to suppress noise and the task-unrelated background EEG and project out the task-relevant EEG saliently, i.e. improve the signal-to-noise ratio. In EEG systems, electrodes on the scalp measure electrical activity of the brain. The EEG signals contain data and patterns of data associated with brain activity. A classifier is used to analyze the EEG signals to infer the existence of certain brain states.

In US Pub No. 2007/0185697 entitled "Using Electroencephalograph Signals for Task Classification and Activity Recognition" Tan describes a trial-averaged spatial classifier for discriminating operator performed tasks for EEG signals. Recent advances in adaptive signal processing have demonstrated significant single trial detection capability by integrating EEG data spatially across multiple channels of high density EEG sensors (L. Parra et al, "Single trial Detection in EEG and MEG: Keeping it Linear", Neurocomputing, vol. 52-54, June 2003, pp. 177-183, 2003 and L. Parra et al, "Recipes for the Linear Analysis of EEG", NeuroImage, 28 (2005), pp. 242-353)). The linear (LDA) classifier provides a weighted sum of all electrodes over a predefined temporal window as a new composite signal that serves as a discriminating component between responses to target versus distracter stimuli.

A rapid serial visual presentation (RSVP) system for triaging imagery is an example of a single-trial EEG system (A. D. Gerson et al "Cortical-coupled Computer Vision for Rapid Image Search", IEEE Transaction on Neural Systems and Rehabilitation Engineering, June 2006) for stimuli in a constrained environment in that both the presentation of stimuli and the analyst's viewing are carefully controlled. Image clips are displayed to the analyst at a rate of approximately 10 per second and a multi-channel LDA classifier is employed to classify the brain response to the presentation of each image. If a significant response is indicated, the system flags the image clip for closer inspection.

SUMMARY OF THE INVENTION

The present invention provides for measurement of brain responses to stimuli in a free-viewing environment in which the presentation of stimuli is natural to the task, possibly unconstrained, and the operator is allowed to move his or her eyes naturally to perform the task.

This is accomplished in a free-viewing environment in which EEG data is measured of the operator's brain activity from a plurality of electrodes placed on the operator's scalp and the operator's free eye movement is tracked and processed to determine fixation events to stimuli. Each fixation event is used as a marker to time window the EEG data. Each segment of windowed EEG data is processed to determine whether the operator exhibited a significant cognitive response to the stimulus. A cue and time-stamp of the fixation event are output. The cue may be a binary decision output (0/1) or may include a likelihood (e.g. 0-100% or 0-1) and/or a tag classifying the stimulus or the nature of the brain response (e.g. ELAN, P300 or P600 event-related potential (ERP)). The sequence of time stamped cues may be synchronized to the stimuli using either a priori knowledge of the stimuli or other detection of the stimuli. The synchronized stimuli and cues may be correlated to further enhance the output. Fixation-locked measurement is a single-trial process in which each fixation produces an output.

In an embodiment, the windowed EEG data is provided to a classifier that performs single-trial detection of patterns of extracted features to classify whether a significant brain response occurred and generate the cue. One approach is to use a single multi-channel classifier that spans the entire time window. Another approach is to use a single multi-channel spatial classifier that spans a narrower window at a known offset from the onset of fixation. Yet another approach is to use a spatio-temporal classifier that comprises a plurality of multi-channel spatial sub-classifiers and a temporal classifier.

Each multi-channel sub-classifier is trained to detect spatial patterns of extracted features during a specific narrow window offset from fixation. Each window has a different offset and together they span the entire window. The temporal classifier combines the outputs of the spatial sub-classifiers to detect temporal patterns across the different time windows relating to the evolution of the non-stationary brain response to stimuli and generate a cue indicative of the occurrence or absence of significant brain response.

In an embodiment, the classifier may be configured to detect pre-fixation stimuli, post-fixation stimuli or both. Pre-fixation stimuli are visual stimuli in the periphery of vision or non-visual stimuli such a sounds, smells, vibrations, sense of fear etc. that trigger a brain response prior to visual fixation. The operator perceives the stimuli, saccades toward the perceived location of the stimuli and then fixates. In this case, the cognitive response of detection occurs while the eyes are moving and recognition occurs after fixation. Post-fixation stimuli are visual stimuli that the operator fixates on and which in turn trigger the brain response. The cognitive responses of detection and recognition both occur after fixation. A robust classifier capable of detecting both pre- and post-fixation stimuli may split the window into pre- and post-fixation windows, process the EEG data using sub-classifiers trained for the respective windows and fuse the results. The pre-fixation locked sub-classifier may be trained based on the assumption of a pre-fixation stimulus. The post-fixation locked sub-classifier may be a single sub-classifier that is trained for both pre and post-fixation stimuli. Alternately, if the system is capable of determining the nature of the stimuli a sub-classifier trained specifically for that type of stimuli may be selected.

In an embodiment, the measurements of the free eye movement may be used to provide additional saccade metrics that may be fused with the cognitive response cues. These saccade metrics may include where the operator is looking, the overall pattern of eye movement, duration of fixation, the length of the saccade, direction of the saccade and persistence of fixation in an approximate direction.

These and other features and advantages of the invention will be apparent to those skilled in the art from the following detailed description of preferred embodiments, taken together with the accompanying drawings, in which:

BRIEF DESCRIPTION OF THE DRAWINGS

FIGS. 5a and 5b are diagrams illustrating pre- and post-fixation stimuli and the cognitive responses of detection and recognition;

FIGS. 7a and 7b are respectively a diagram illustrating a sequence of windowed EEG data locked to the sequence of fixations and the sequence of cognitive response cues and time-codes;

DETAILED DESCRIPTION OF THE INVENTION

The present invention provides fixation-locked measurement of brain response to task-relevant stimuli in a free-viewing environment. The free-viewing environment is one in which the presentation of stimuli is natural to the task and the operator is allowed to move his or her eyes naturally to perform the task. Fixation-locked measurement generates cues indicative of whether an operator exhibited a significant cognitive response to task-relevant stimuli. The sequence of cues are time-coded and synchronized to the associated fixation.

The sequence of time-coded cues may be used to cue a system response or to augment system responses. Response based cueing or augmentation may be used in a wide variety of consumer, security and warfare environments in which relevant stimuli produce strong cognitive responses. For example, in a language learning environment both text (visual stimuli) and audio (non-visual stimuli) learning materials may be presented to a student. The sequence of time-coded cues may be synchronized to the presentation of the materials to assess a student's mastery of the materials. These cues may be used to modify the presentation or content of the learning materials. In an urban combat environment, stimuli (visual or non-visual) occur randomly or asynchronously. The cues may be used to alert weapon systems or other soldiers. The sequence of time-coded cues may be correlated and synchronized to visual or non-visual stimuli detected by other means such as imaging or acoustic sensors.

Without loss of generality, our approach will be presented for an operator (warfighter) in an urban combat environment. The stimuli (visual or non-visual) occur randomly or asynchronously in both time and position with respect to the operator. The operator freely moves his or her eyes during the mission and in response to the occurrence of stimuli.

Figure 1:
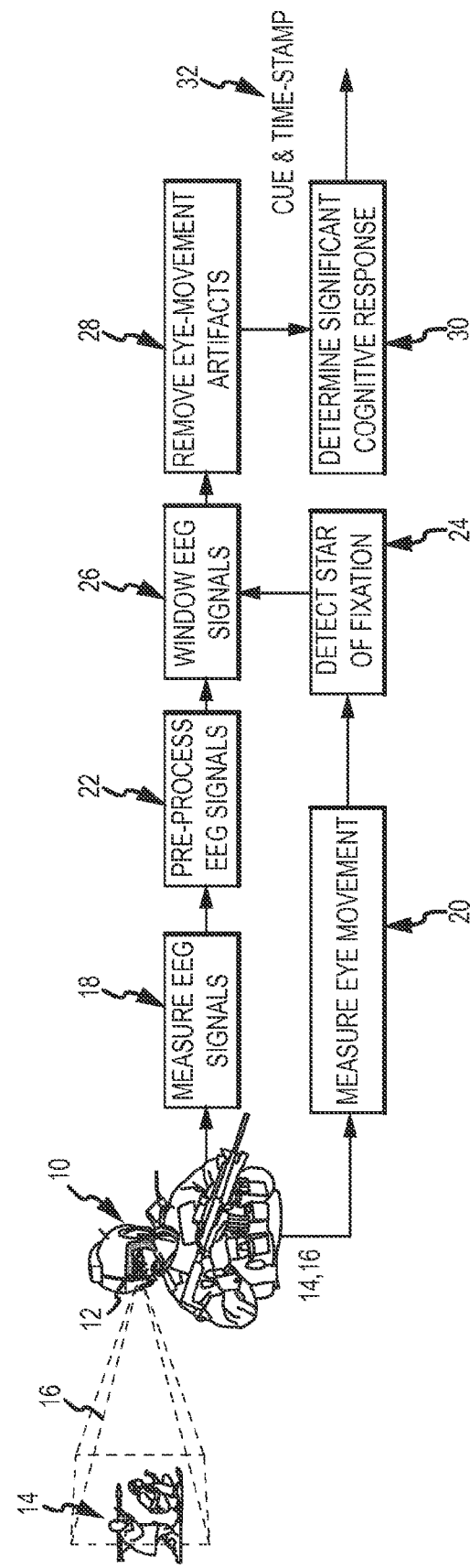
FIG. 1 is a flow diagram of fixation-locked measurements of brain responses to determine significant cognitive responses to stimuli.

As shown in FIG. 1, an operator 10 outfitted with a cognitive monitoring device (CMD) 12 for monitoring, classifying and transmitting cues based on the operator's cognitive responses to stimuli is on patrol in an urban combat environment. The CMD is also configured to monitor eye movement and determine fixation on a relevant stimulus 14 in the operator's field-of-view (FOV) 16. Relevant stimuli can be any visual or non-visual stimuli that trigger a strong cognitive response. The stimuli may include pre or post-fixation or both. For example, a terrorist with a rocket propelled grenade (RPG), an explosion or an odor are examples of relevant visual and non-visual stimuli. Some stimuli may trigger a strong response but are not relevant to the task. For example, children chasing a camel down the street or the sound of a car back firing. Other stimuli may only trigger weak responses. The CMD may also be configured with other sensory capabilities such as a GPS receiver to determine the operator's location or acoustic sensors or imaging sensors.

As the operator 10 scans the environment, CMD 12 measures the operator's EEG signals (step 18) and eye movement (step 20). The EEG signals may be pre-processed (step 22) to remove large artifacts such as those from eye blinks and head movements and band pass filtered to reduce noise. The operator's eye movement is monitored to detect the start of fixation e.g. a "fixation event" (step 24). Each fixation event provides a marker to time window the EEG signals (step 26). The windowed EEG signals are suitably processed to reduce artifacts and mitigate noise due to eye movement (step 28). Each time segment of fixation-locked windowed EEG signals is processed to determine if there is a significant cognitive response to a relevant stimulus (step 30). Fixation-locked measurement is a single-trial process in which each fixation produces an output cue. The sequence of cues 32 are time-stamped with the associated fixation-event. The cue may be a binary decision (0 or 1) or assigned a likelihood (0-1 or 0 to 100%) that a significant cognitive response occurred. The cue may be a generic indicator of cognitive response or may include a tag classifying the stimulus or the nature of the brain response. For example, the tag might indicate the particular ERP (e.g. ELAN, P300, P600).

Figure 2:
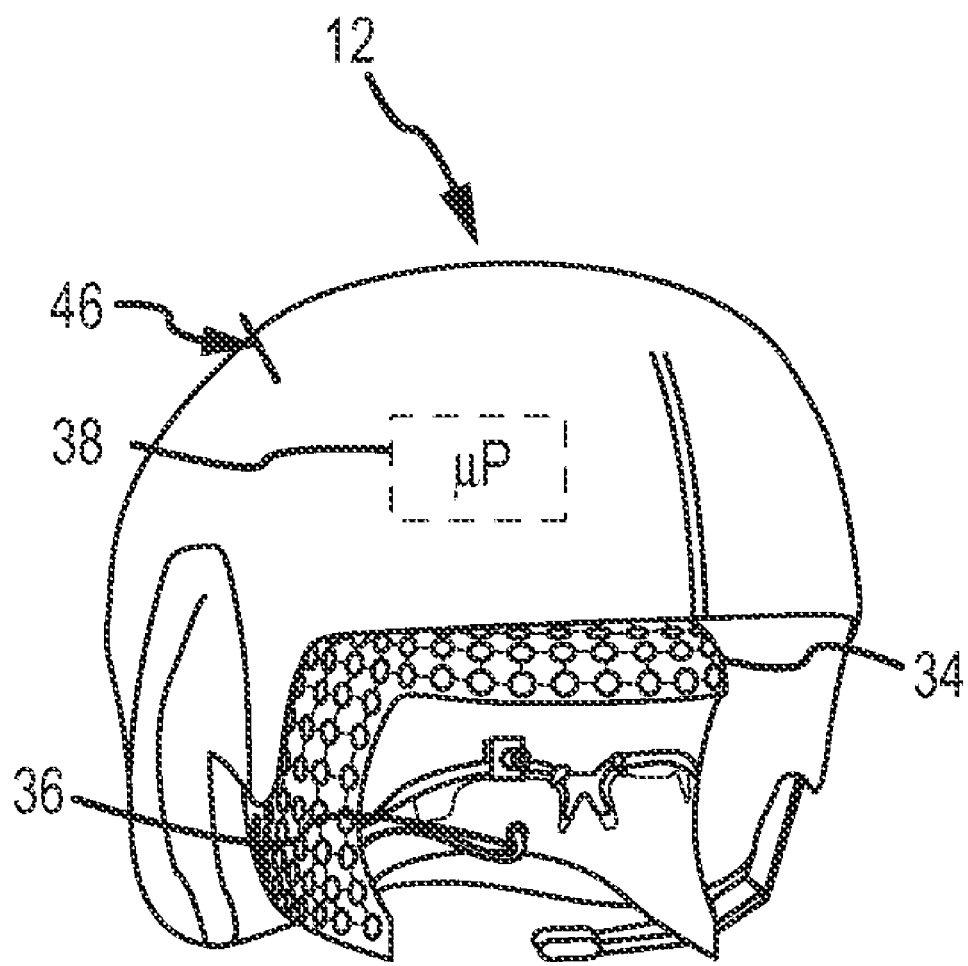
FIG. 2 is a diagram of a cognitive monitoring device (CMD)
Figure 3:
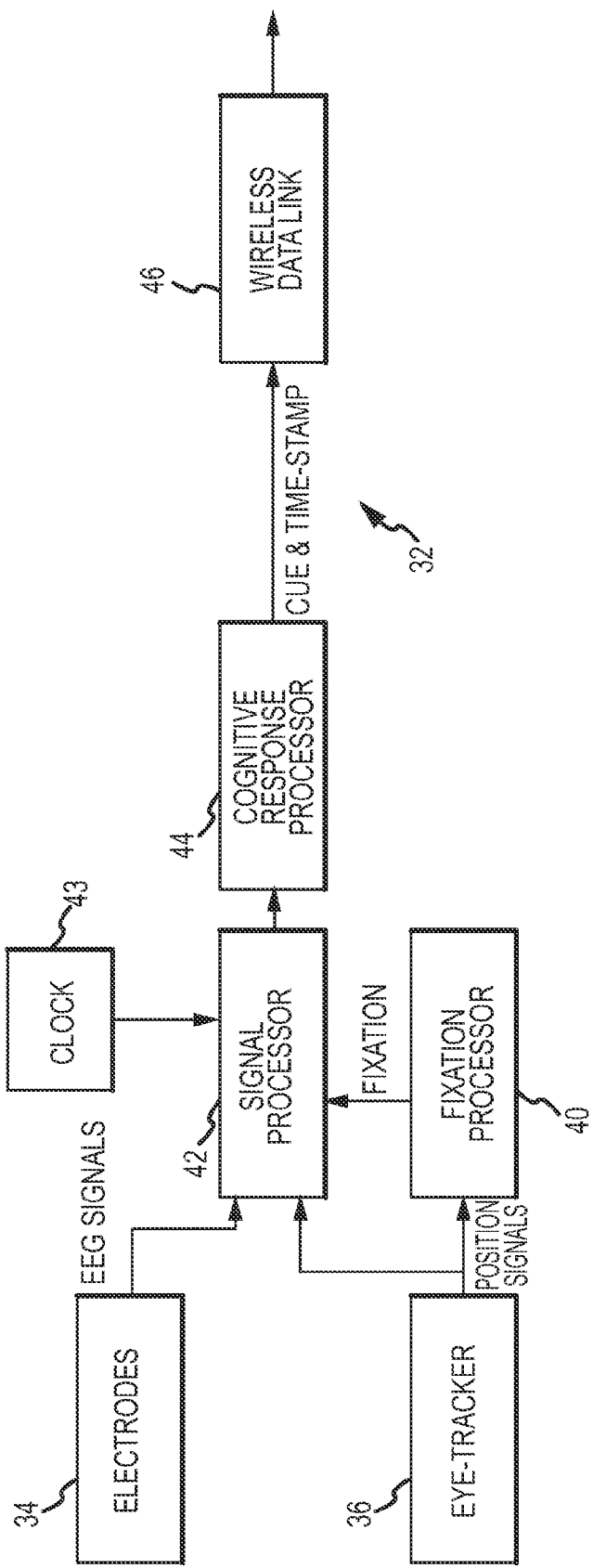
FIG. 3 is a hardware block diagram.

An embodiment of CMD 12 is depicted in FIGS. 2 and 3. In this configuration, the CMD includes electrodes 34 placed on the operator's scalp to generate multiple spatial channels of EEG signals, each spatial channel including a high-resolution temporal signal typically representative of an amplitude difference between a pair of electrodes. An eye-tracker 36 measures the instantaneous position of the eyes by detecting the pupil (as the detection of light reflected off the back of the retina due to the NIR light projected onto the eye). The measure of the diameter may provide pupil size signals. The measure of the position of the eyes provides the position signals. With the position sampled at high rates, one can determine the instantaneous displacement. If the displacement, measured as a change in position or derivatives such as the velocity, surpasses a reasonable small threshold, it means that the eyes are moving. A resumption of the stable position indicates a fixation.

Although it is understood that all processing could be integrated into a single processor 38 as shown in FIG. 2 or allocated among a plurality of processors in a variety of ways, for clarity signal processing is divided among several functional processors in FIG. 3. A fixation processor 40 monitors the position signals to determine fixation on a particular stimulus. Fixation occurs when the eyes remain focused on a constrained spatial region of, for example, less than half a degree. A signal processor 42 pre-processes the raw EEG signals using the position signals to remove artifacts due to blinks and head movement, segments the signals into a sequence of fixation-locked time windows (possibly overlapping) and processes each segment of EEG data to reduce eye movement artifacts noise. Artifact removal for head movement and blinks is well known. A technique for removal of blink artifacts is described in Lucas C. Parra et al. "Response Error Correction—A Demonstration of Improved Human-Machine Performance Using Real-Time EEG monitoring" IEEE Trans. On Neural Systems and Rehabilitation Engineering, Vol. 11, No. 2, June 2003, which is hereby incorporated by reference. A technique for removal of eye movement artifacts is described in German Gomez-Herrero "Automatic Removal of Ocular Artifacts in the EEG without an EOG Reference Channel", Proc. of the $7^{th}$ Nordic Sig. Proc. Symp., pp. 130-133, 7-9 Jun. 2006, which is hereby incorporated by reference. A clock 43 provides a clocking signal the signal processor uses to assign a time-stamp to each signal sample and fixation. A cognitive response processor 44 extracts features from each segment of windowed EEG data and classifies the data to provide a cue and time-stamp 32. The cue and time-stamp may be transmitted via a data link 46 to cue or augment a system. In our example, a command a control system may use the cue to alert other operators or to cue a weapons system.

Many environments and applications dictate single-trial detection of the significant brain responses. Without the benefit of multi-trial averaging to improve SNR reliable detection of significant brain responses can be difficult. This is particularly true in an environment in which the presentation of the stimuli is not tightly constrained and the operator is not constrained to view the stimuli in a fixed location. Fixation-locked measurement allows for single-trial detection of significant brain responses in natural or less constrained environments.

Figure 4:
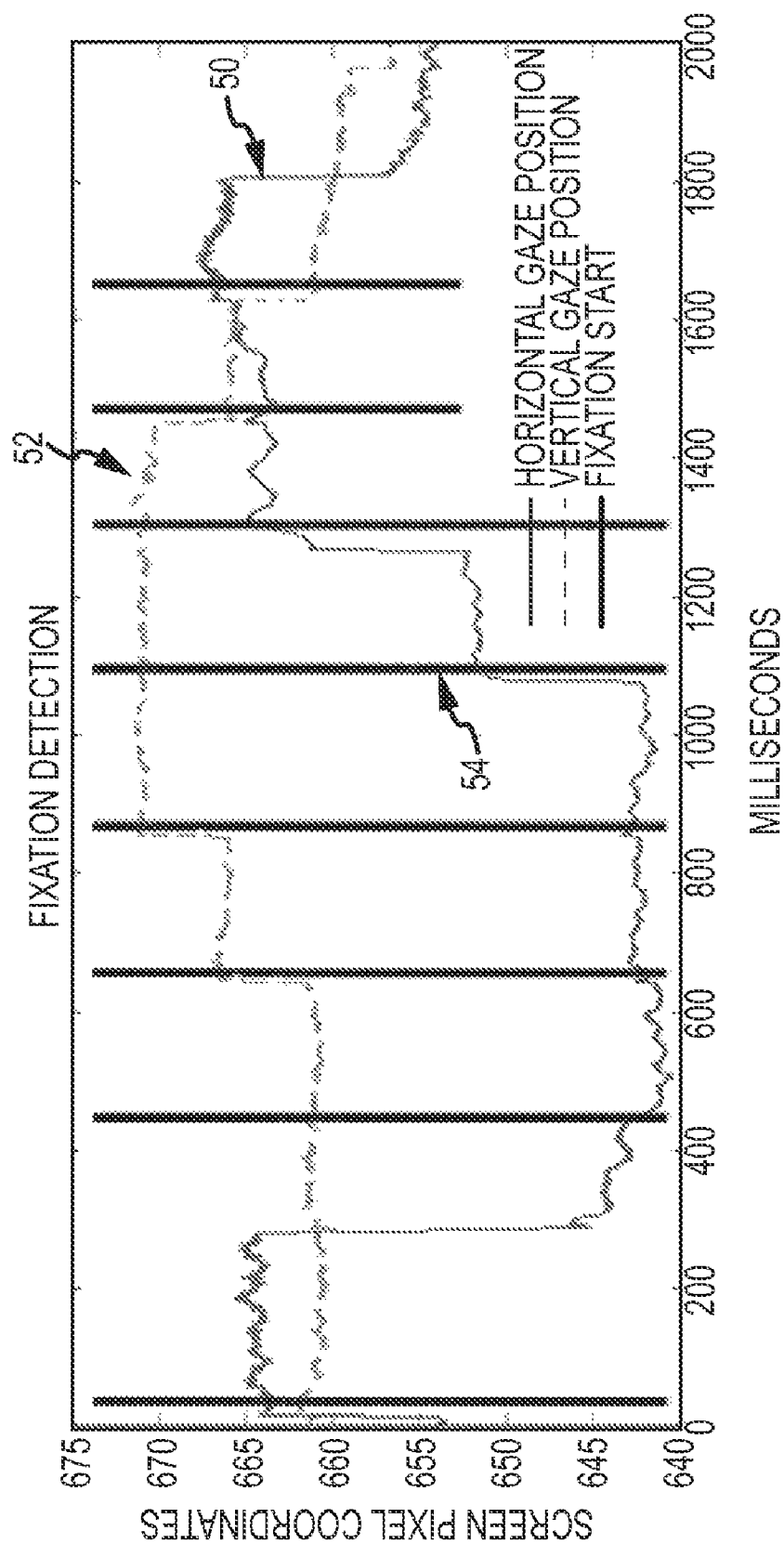
FIG. 4 is a plot of horizontal and vertical gaze position to natural stimuli over time illustrating the onset of fixation.

Referring now to FIG. 4, the eye tracker provides position signals for horizontal and vertical gaze position 50 and 52, respectively. Eye movement indicated by the change in displacement of either the horizontal or vertical gaze position followed by a resumption of a stable position indicates fixation. The rapid movement from one stable position to the next stable position indicates the start of a fixation event 54. The human eye is incapable of fixating on any one position for more than a few hundred milliseconds. On average in a 1000 ms window the eye will move three to five times. Even if an operator is staring in one direction the eyes will move position albeit a small displacement (known as microsaccades or microtremor) causing a sequence of fixations in approximately the same direction.

Referring now to FIGS. 5a and 5b, fixation can be categorized as either pre-fixation or post-fixation depending on whether the relevant stimulus triggers the initial brain response before or after fixation on that relevant stimulus. As shown in FIG. 5a, pre-fixation stimuli 60 are visual stimuli in the periphery of vision or non-visual stimuli such a sounds, smells, vibrations, sense of fear etc. while the operator is fixated 62 on something else. The pre-fixation stimuli trigger a brain response prior to fixation on or in response to the relevant stimulus. The operator perceives the stimuli 40, moves his or her eyes toward the perceived location (saccade 64) of the stimuli and then fixates 66 on that stimulus if visual or in the perceived direction of the stimulus if non-visual. In this case, the cognitive response of detection 68 occurs while the eyes are moving and recognition 70 occurs after fixation. As shown in FIG. 5b, post-fixation stimuli 72 are visual stimuli that the operator fixates on and which in turn trigger the brain response 74. The cognitive responses of detection 76 and recognition 78 both occur after fixation. To detect significant cognitive responses to both types of stimuli it may be useful for the window to encompass EEG signals both before and after fixation on the stimulus that triggers the cognitive brain response.

Figure 6A:
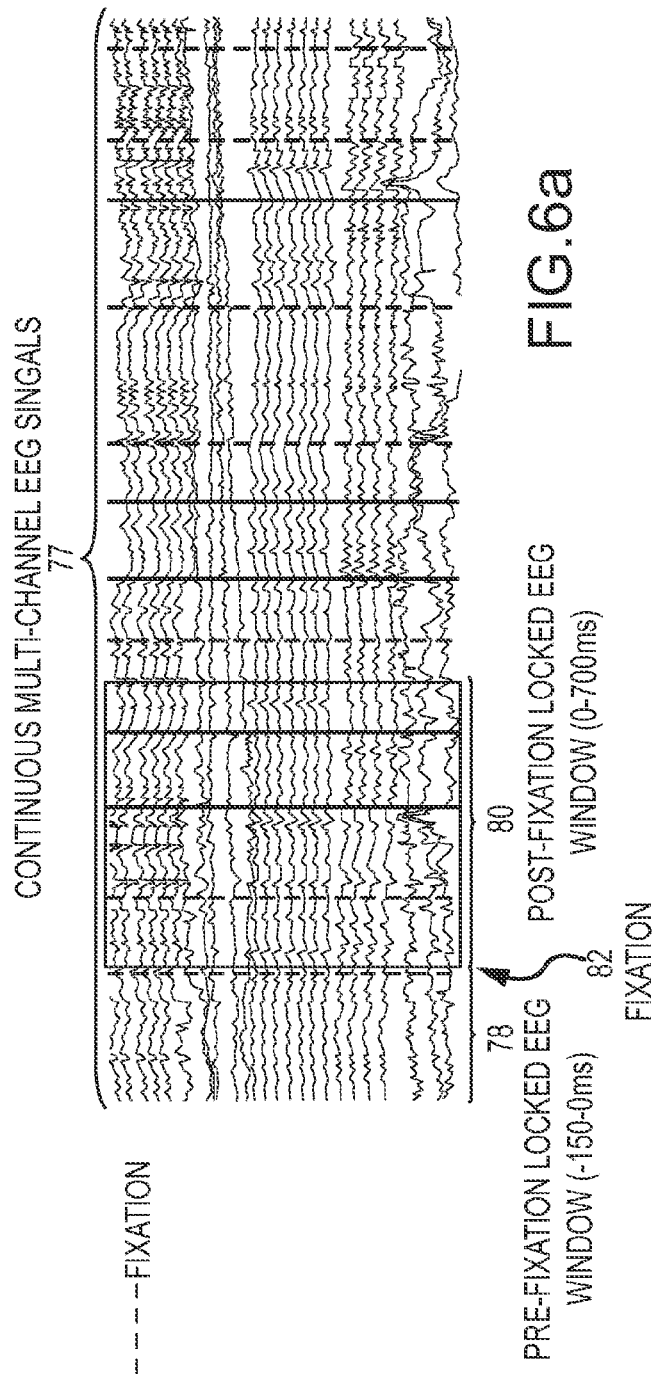
FIGS. 6a and 6b are respectively a diagram of pre-fixation and post-fixation locked EEG windows in continuous multi-channel EEG signals and a block diagram of the fusion of the pre-fixation and post-fixation locked sub-classifiers.
Figure 6B:
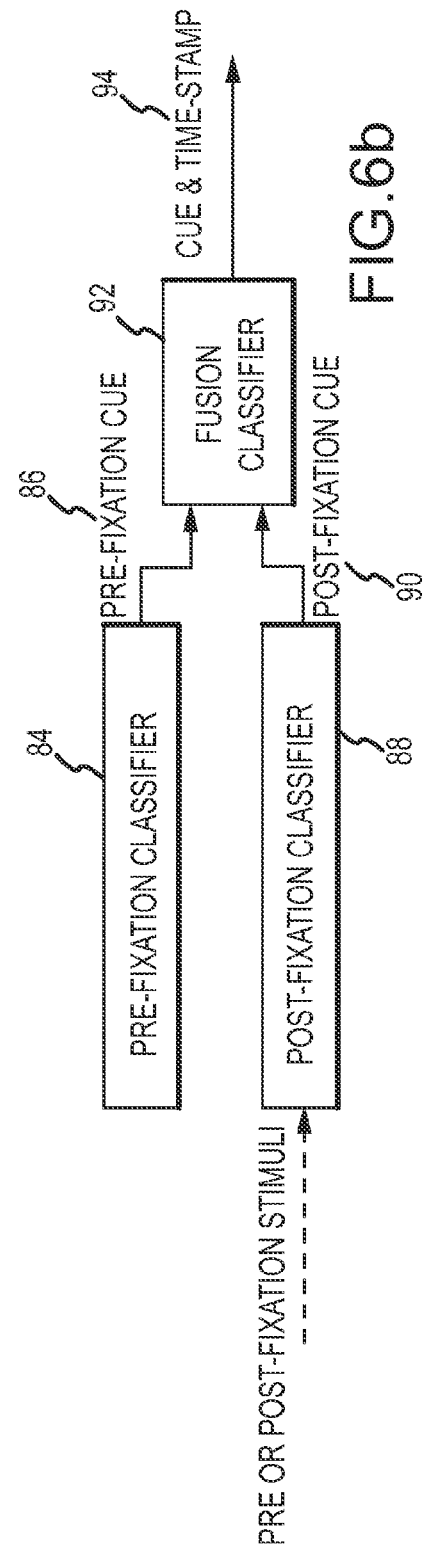

Referring now to FIGS. 6a and 6b a robust classifier capable of detecting both pre- and post-fixation stimuli in multi-channel EEG signals 77 may split the window into a pre-fixation window 78 and a post-fixation window 80 around fixation event 82. The nature of brain activity, hence the collected EEG signals, is different during saccades and during fixation. The pre-fixation window 78 may cover the time period of −300 ms to 0 ms and the post-fixation window 80 may cover the time period from 0 ms to 700 ms relative to fixation event 82. The extent of either window may vary dependent upon the application or the classifier used to characterize the cognitive response.

The EEG signals in the pre-fixation window 78 are presented to a pre-fixation locked sub-classifier 84. This classifier is trained to look for patterns of brain activity indicative of a stimulus that causes the operator to move his or her eyes towards the perceived stimulus during which the function of detection is performed. The classifier generates a pre-fixation cue 86, typically indicating the likelihood that a significant cognitive response has occurred. The EEG signals in the post-fixation window 80 are presented to a post-fixation locked sub-classifier 88. The post-fixation locked sub-classifier is trained to look for patterns of brain activity that occur after fixation on the stimulus that are indicative of significant cognitive response. The post-fixation locked sub-classifier may be a single classifier that is trained for both pre and post-fixation stimuli. Alternately, if the system is capable of determining the nature of the stimuli a classifier trained specifically for that type of stimuli may be selected. The classifier generates a post-fixation cue 90, typically indicating the likelihood that a significant cognitive response has occurred. A fusion classifier 92 processes the pre- and post-fixation cues 86 and 88 and generates a single cue 94, typically indicating the likelihood or binary decision of a significant cognitive response pair with the time-code of the fixation event. The fusion classifier is trained to look for patterns in the pre and post-fixation locked cues indicative of significant cognitive response.

Referring now to FIGS. 7*a* and 7*b*, the operator's eye movement signals are processed to determine a sequence of fixation events 100 that are synchronized to the multi-channel EEG signals 102. Each fixation event provides a marker for applying a window 104 (e.g. the pre and post-fixation windows) to segment the EEG signals. Each segment of EEG signals constitutes a single-trial on which fixation-locked measurements are performed to generate a cue that is output with a time-code of the associated fixation event. In an embodiment, every fixation event generates a cue 106 having an associated likelihood 108 and time-stamp 110. Weak cognitive responses are represented by a low likelihood or binary decision 0 and strong cognitive responses by a high likelihood or binary decision 1.

EEG Classifier

Electroencephalography (EEG) is the neurophysiologic measurement of the electrical activity of the brain recording from electrodes placed on the scalp of the operator. The EEG signals contain data and patterns of data associated with brain activity. A multi-channel spatial classifier analyzes the fixation-locked windowed EEG signals to detect significant brain responses to task-relevant stimuli. The integration of EEG data spatially across multiple channels improves the SNR much like trial-averaging.

An event-related potential (ERP) is a measured brain response that is the result of a thought or perception that can be linked to an event. More formally, it is any stereotyped electrophysiological response to an internal or external stimulus. While evoked potentials reflect the processing of the physical stimulus, event-related potentials are caused by the brain processes, that might involve perception, memory, expectation, attention, or changes in the mental state, among others. Though some ERP components are referred to with acronyms (e.g., early left anterior negativity—ELAN), most components are referred to by a preceding letter indicating polarity followed by the typical latency in milliseconds. Thus, the N400 ERP component is described as a negative voltage deflection occurring approximately 400 ms after stimulus onset, whereas the P600 component describes a positive voltage deflection 600 ms after stimulus onset. The stated latencies for ERP components are often quite variable; for example, the N400 component may exhibit a latency between 300 ms-500 ms.

The classifier can, for example, be constructed to extract features (e.g. time domain such as amplitude and/or frequency domain such as power) from one or more time windows and render a likelihood output (continuous value from 0 to 1) or decision output (binary value of 0 or 1) based on a weighted (linear or non-linear) combination of the features. Typical classifiers include the LDA, support vector machine (SVM), neural networks or AdaBoost. A rich set of features may be available from which a smaller subset of features are selected for a particular application based on training. The classifier is trained based on the extracted features to detect a significant brain response for a single-trial relevant stimulus. The classifier may be trained to recognize any significant brain response or, more typically, it may be trained to recognize significant brain response for particular relevant stimuli and reject significant brain responses for non-relevant stimuli. Separate classifiers may be used for the pre-fixation and post-fixation windows.

Figure 8:
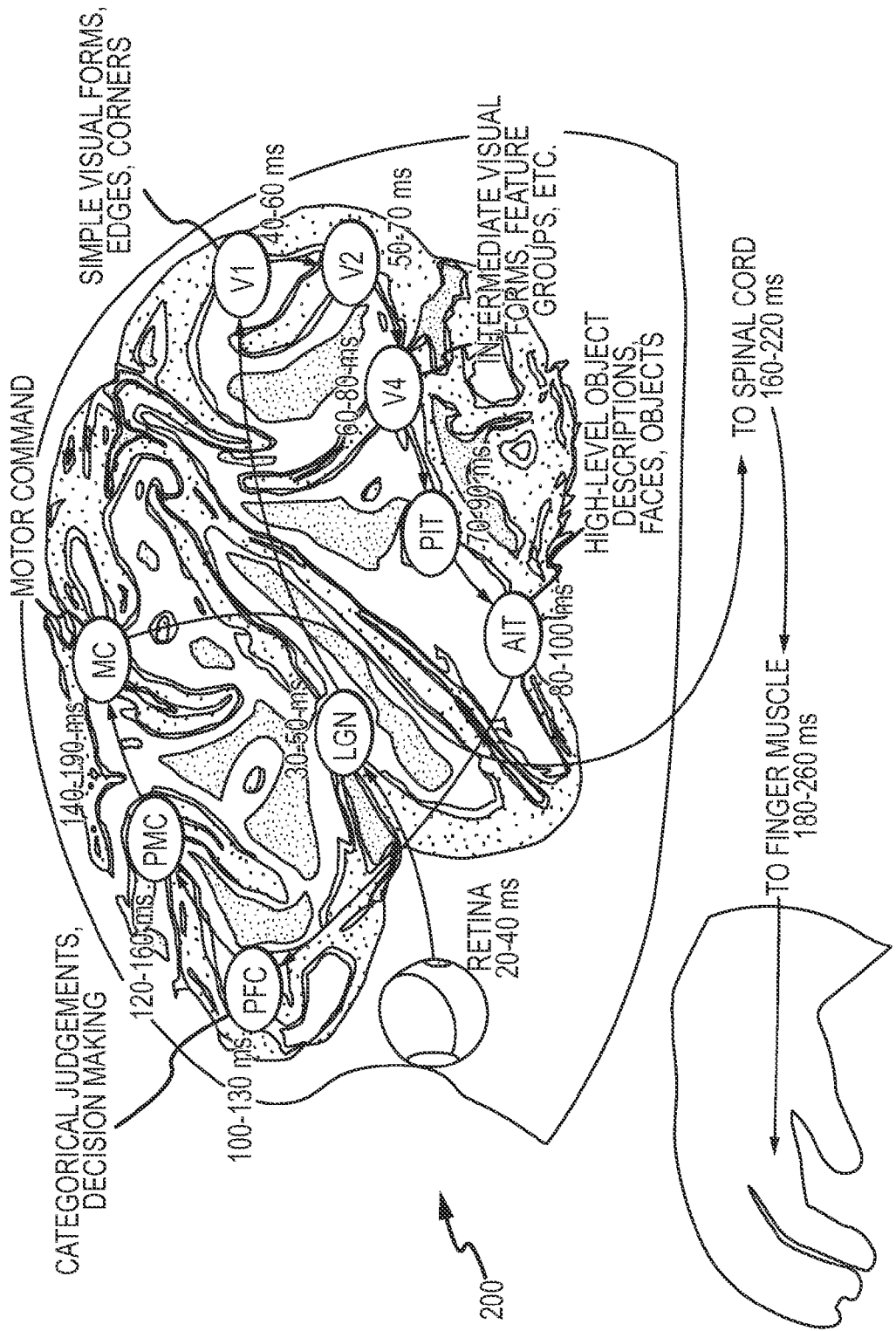
FIG. 8 is a diagram of a primate's brain illustrating the non-stationary brain response in response to a stimulus.

The brain response to stimuli is not a stationary pulse. The brain response reflects neurophysiological activities located in selectively distributed sites of the brain evolving with a continuous time course. FIG. 8 illustrates the evolving brain response 200 in a primate, which would be similar to a human. The precise timing will vary between human and primate and from human subject to human subject. In human subjects, the first indication of brain response to a stimuli occur approximately 80 ms after the onset of the stimuli and may continue for up to approximately 900 ms-1.5 sec as the signal propagates through different areas of the brain.

The brain response to "task-relevant" information is a non-stationary signal distributed across multiple areas of the brain. Specifically, perceptual information from the senses is first processed in primary sensory cortex from where it travels to multiple cortical mid-section areas associated with separately processing the spatial ("Where") and semantic ("What") meaning of the information. The resulting information patterns are matched against expectations, relevance or mismatch at which point signals are relayed to more frontal regions were higher-level decisions can be made about the relevance of the information. If enough evidence exists, a commitment to respond is then made. This suggests that the decision process involves multiple sites (space) across a relative long time window (and time).

Depending in large part on the nature of the environment in which the stimuli are presented to the operator, the Classifier may be configured in many different ways. Each fixation-event may be used as a marker to extract a window of data that is presented to a single multi-channel spatial classifier. Alternately, each fixation event may be used as a marker to extract a pre-fixation window of data that is presented to a pre-fixation locked sub-classifier and to extract a post-fixation window of data that is presented to a post-fixation locked sub-classifier and the respective outputs fused to produce the final output. Each of the pre-fixation locked and post-fixation locked sub-classifiers may be configured as a single multi-channel spatial classifier that spans the entirety of the window, a single multi-channel spatial classifier that spans a narrower window having a specific offset to the fixation event or a spatio-temporal classifier that includes multiple spatial classifiers that correspond to different narrow windows having different offsets from the fixation event and a temporal classifier that detects temporal patterns in the outputs of the multiple spatial classifiers. The spatio-temporal classifier attempts to capture the spatio-temporal pattern that evolves as a cognitive brain response progresses through the brain in response to a relevant stimulus by collecting evidence of this non-stationary signal and combining it to improve detection confidence. For example, the spatial classifiers may roughly correspond to certain ERPs and the temporal classifier to temporal patterns of the ERPs. In an embodiment, the pre-fixation locked sub-classifier may be a single multiple channel classifier that spans the pre-fixation window and the post-fixation locked sub-classifier may be a spatio-temporal classifiers whose multiple narrow windows span the post-fixation window.

The classifier may be configured to output a cue, either a binary decision or a likelihood, that a significant brain response has occurred. The classifier may be configured to only generate the cue with a binary 1 or high likelihood if a significant brain response has occurred in response to a specific task-relevant stimulus. The classifier may be configured to generate a cue including a tag classifying the stimulus or the nature of the brain response (e.g. ELAN, N300, P600, etc.). The human brain can exhibit a significant response in different ways and for different reasons.

Spatio-Temporal Classifier

Figure 9:
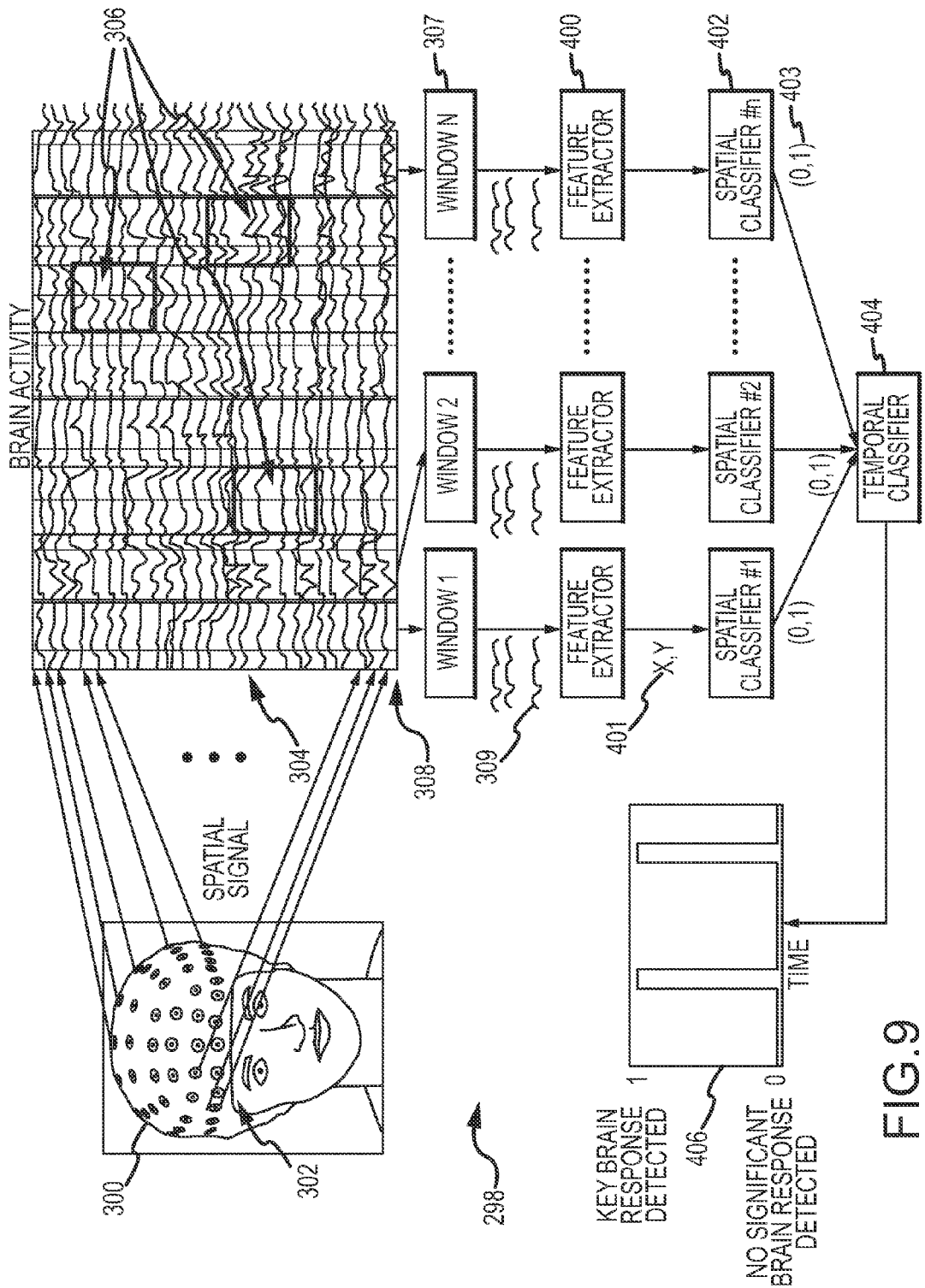
FIG. 9 is a block diagram of a spatio-temporal classifier configured to exploit the non-stationarity properties of human brain response.

Referring now to FIG. 9, a spatio-temporal classifier 298 is configured as the post-fixation locked sub-classifier. The classifier is trained to detect significant brain responses for either pre-fixation or post-fixation stimuli and generate the appropriate cue. The pre-fixation locked sub-classifier may also comprise a spatio-temporal classifier.

Electrodes 300 on a subject's scalp 302 generate multiple spatial channels of EEG data 304 in response to various stimuli. Each spatial channel includes a temporal signal 306 typically representative of an amplitude difference between a pair of electrodes. Unlike other methods of detecting brain responses such as MRI, EEG data has a very fine time resolution. To detect significant brain responses to task-relevant stimuli, we configure the classifier to capture the evolving spatio-temporal pattern as the response to the stimuli propagates through certain distributed areas of the brain. In general, the classifier is not classifying the stimulus itself but is deciding whether a significant brain-response has occurred. The classifier may be trained to detect any significant brain response or it may be trained to detect significant brain responses for certain types of task-relevant stimulus e.g. certain targets of interest in images. The classifier may be trained to classify different types or classes of stimulus.

The EEG data is subdivided into a plurality of windows 307 starting at the fixation event 308 (t=0 ms) sufficient to capture the temporal evolution of the brain response to a pre or post-fixation stimulus (e.g. 700 ms). Each window contains a different temporal segment of data 309 offset from the onset of fixation event 308 for a subset, typically all, of the spatial channels. In order to detect temporal patterns across the different time windows it is useful to control four separate parameters; the window duration, the number of windows, the total temporal window captured and the overlap between windows. The window duration and overlap are typically uniform but could be tailored based on specific training for certain applications. Window duration may be in the range of 20-200 ms and more typically 50-100 ms; long enough to capture signal content with sufficient SNR yet short enough to represent a distinct portion of the non-stationary signal. The number of windows must be sufficient to provide a robust temporal pattern. The total temporal window typically spans the onset of the stimuli to a threshold window beyond which the additional data does not improve results. The threshold may be assigned based on the response of each subject or based on group statistics. The threshold window for most subjects for our experimental stimuli is near 500 ms. Window overlap is typically 25-50%, sufficient to center critical brain response transitions within windows and to provide some degree of temporal correlation between spatial classifiers. Larger overlaps may induce too much correlation and become computationally burdensome. The number of windows, position and duration may be selected to correspond to particular ERPs. Knowledge of the environment, nature of the stimuli and the ERPs invoked by the stimuli may be used to optimize the classifier.

Feature extractors 400 extract features X, Y, ... 401 from the respective windows of EEG data. These features may be time-domain features such as amplitude or frequency-domain features such as power or combinations thereof. Features may include signal amplitude, absolute amplitude, short moving average, instantaneous power in a specific frequency range, etc. The extracted features may or may not be the same for each window. To optimize performance and/or reduce the computational load, the nature and number of features will be determined during classifier training, typically for a particular task-relevant application. For example, classifier training may reveal that certain features are better discriminators in early versus late windows. Furthermore, since the temporal evolution of the signal roughly corresponds to its propagation through different areas of the brain features may be extracted from different subsets of spatial channels for the different windows. Training would identify the most important spatial channels for each window.

Once extracted, the features from the different temporal windows are presented to respective spatial sub-classifiers 402. Each sub-classifier is trained based on the extracted features for its particular window to detect a significant brain response for a task-relevant stimulus. The sub-classifier may be trained to recognize any significant brain response or, more typically, it may be trained for a particular task such as image target recognition, word recognition, threat detection, etc. Brain activity is measured and recorded during periods of task relevant and irrelevant stimulation and the sub-classifiers are trained to discriminate between the two states. Specific techniques for training different classifiers are well known in the art. A linear discrimination analysis (LDA) classifier of the type used in single-window RSVP systems was configured and trained for each of the N spatial classifiers. The LDA classifier described by Parra linearly combines the multiple spatial EEG channels to form an aggregate representation of the data. Other linear and non-linear classifiers such as support vector machines (SVM), neural networks or AdaBoost could also be employed. Different sub-classifiers may be used for the different windows. Each sub-classifier 402 generates a first level output 403. The sub-classifiers may be configured to generate either a likelihood output e.g. a continuous value from 0 to 1, or a decision output e.g. a binary value of 0 or 1 depending on the type of fusion used to combine the outputs.

The spatial sub-classifiers' first level outputs are presented to a temporal classifier 404 that combines them to detect temporal patterns across the different time windows relating to the evolution of the non-stationary brain response to task-relevant stimulus and to generate a second level output 406 indicative of the occurrence or absence of the significant non-stationary brain response. In this configuration, the second level output is a binary decision as to the brain state for a current stimulus. Although there is some latency due to data collection e.g. 500 ms from the onset of the fixation event, the processing time is small, approximately 5 ms, so that the system can generate decision level outputs in real-time that keep up with the presentation or occurrence of stimuli. Alternately, the second level output may be a continuous value form 0 to 1 indicative of the likelihood (e.g. 0-100%) of significant cognitive response Feature-level fusion detects the temporal pattern using a global classifier such as a LDA or a relevance vector machine (RVM). The continuous valued outputs of the spatial classifiers are considered as inputs features. For the LDA classifier, let y be the observed vector of spatial classifier output, a weight vector W can be derived based on training data to generate a one-dimension projection $z=W^T y$ where the dimension of the weight vector W is the number of spatial classifiers M. The projection z serves as an estimate of global pattern. The likelihood that a measurement belongs to the target class is assumed to follow a logistic distribution e.g. $p(H_1|y)=1/(1+e^{-z})$. Receiver operating characteristic (ROC) curves can be obtained by comparing $p(H_1|y)$ to a threshold $\eta$ having a value in [0,1]. The decision rule can be $p(H_1|y) \geq \eta$, out=1 and $p(H_1|y) \leq \eta$, out=0 or vice versa where out=1 represent a classifier's decision to declare detection of significant brain response and out=0 represents a classifier's decision to declare a non-significant brain response. When real data is presented to the temporal classifier, the weigh vector W will combine the outputs to discriminate patterns that indicate significant brain response from those that do not.

A RVM classifier models the likelihood that a measurement belongs to the target class as a sigmoid logistic function distribution $p(H_1|y)=1/(1+e^{-f_{RVM}(y)})$ where $f_{RVM}(y) \Sigma(\alpha_i K(y, y_i)+b)$ for i=1 to M where $K(y,y_i)$ is the kernel function, $\alpha_i$ is the weight parameter for each spatial classifier output and b is a threshold. To determine the $\alpha_i$ using a Bayesian approach, they are encoded to have a sparse prior: statistically independent from each other and follow a zero-mean, Gaussian distribution with variance $\lambda_i^{-1}$; in addition, a gamma distribution is assumed on the hyper-parameter $\lambda_i$. Therefore, prior $\alpha_i$ are highly concentrated around 0 and generate very few nonzero terms in $f_{RVM}(y)$. A maximum a posteriori (MAP) estimate for the weight parameters $\alpha_i$ can be obtained by maximizing the posterior distribution of the class labels given the training set. The same decision rule can be applied.

Decision-level fusion detects temporal patterns by optimizing complementarities of the spatial sub-classifiers' binary decisions. Decision-level fusion is implemented to achieve an optimal combination of maximum likelihood estimates achievable between two or more alternative and complementary decisions. Training provides the operating points for the decision-level classifier.

An effective approach is to use Bayesian inference where spatial classifiers' binary decisions are treated as multiple hypotheses that need to be combined optimally. The hypotheses are $H_0$ (distractor) and $H_1$ (task-relevant stimulus). The spatial classifier output vector has joint probability density function $P(y_1, \ldots, y_k|H_j)$ under hypothesis $H_j$, for j=0,1 and k=2, ..., M. For individual local amplitude-based classifiers, they receive as inputs the N-dimension observation vector x (amplitude) and make the decisions based on the LDA classifier outputs (given a fixed value of decision threshold). The decisions drawn from M individual spatial classifiers are denoted as $u_k$, where k=1, 2, ... M and $u_k=0$ if the spatial classifier k decides $H_0$ and $u_k=1$ if the spatial classifier k decides $H_1$. Individual classifier's decision $u_k$ depends only on the spatial classifiers' output vectors y.

$$u_k = \alpha(x_k)$$
$$= 0, \text{ spatial classifier } k \text{ decides } H_0$$
$$1, \text{ spatial classifier } k \text{ decides } H_1$$

The performance characteristics of individual classifier k can be specified by $P(u_k|H_j)$, where $P(u_k=1|H_0)=P_{fk}$=the probability of false alarm and $P(u_k=1|H_0)=P_{fk}$=probability of detection.

The global decision fusion classifier receives the decisions of the individual spatial classifiers as its inputs. The decision at the fused level, $$u = \varphi(u_1, u_2, \ldots, u_k)$$
$$= 0, \text{ global decision } H_0$$
$$1, \text{ global decision } H_1$$

Depends only on spatial decision, their probability of detection $P_{dk}$, probability of false alarm $P_{fk}$ and how complementary they are to each other. Since multiple spatial LDA classifiers base their decisions on EEG raw signals in different temporal windows, the simplest assumption is that these decisions are statistically independent.

Classifier Training for Pre- and Post-Fixation Stimuli

A training method is proposed for both the pre- and post-fixation locked sub-classifiers that performs well across a broad range of tasks. The method isolates the critical "detection" cognitive response while a subject performs eye movements from the "recognition" or "detection and recognition" responses that occur after fixation on the task relevant stimulus. The training method simultaneously gathers data for both pre-fixation and post-fixation stimuli.

Figure 10A:
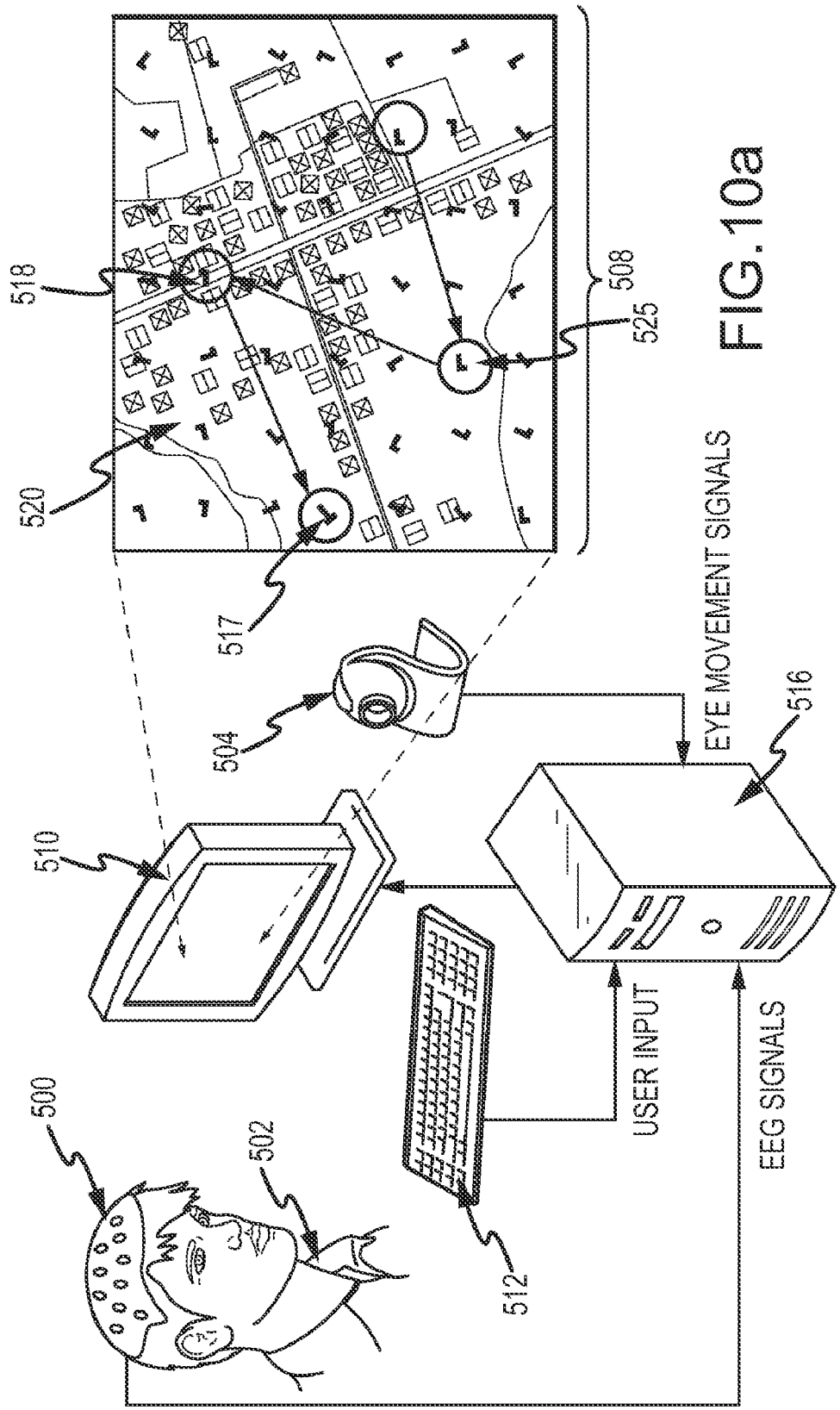
FIGS. 10a and 10b are a hardware and flow diagram illustrating an embodiment for classifier training.
Figure 10B:
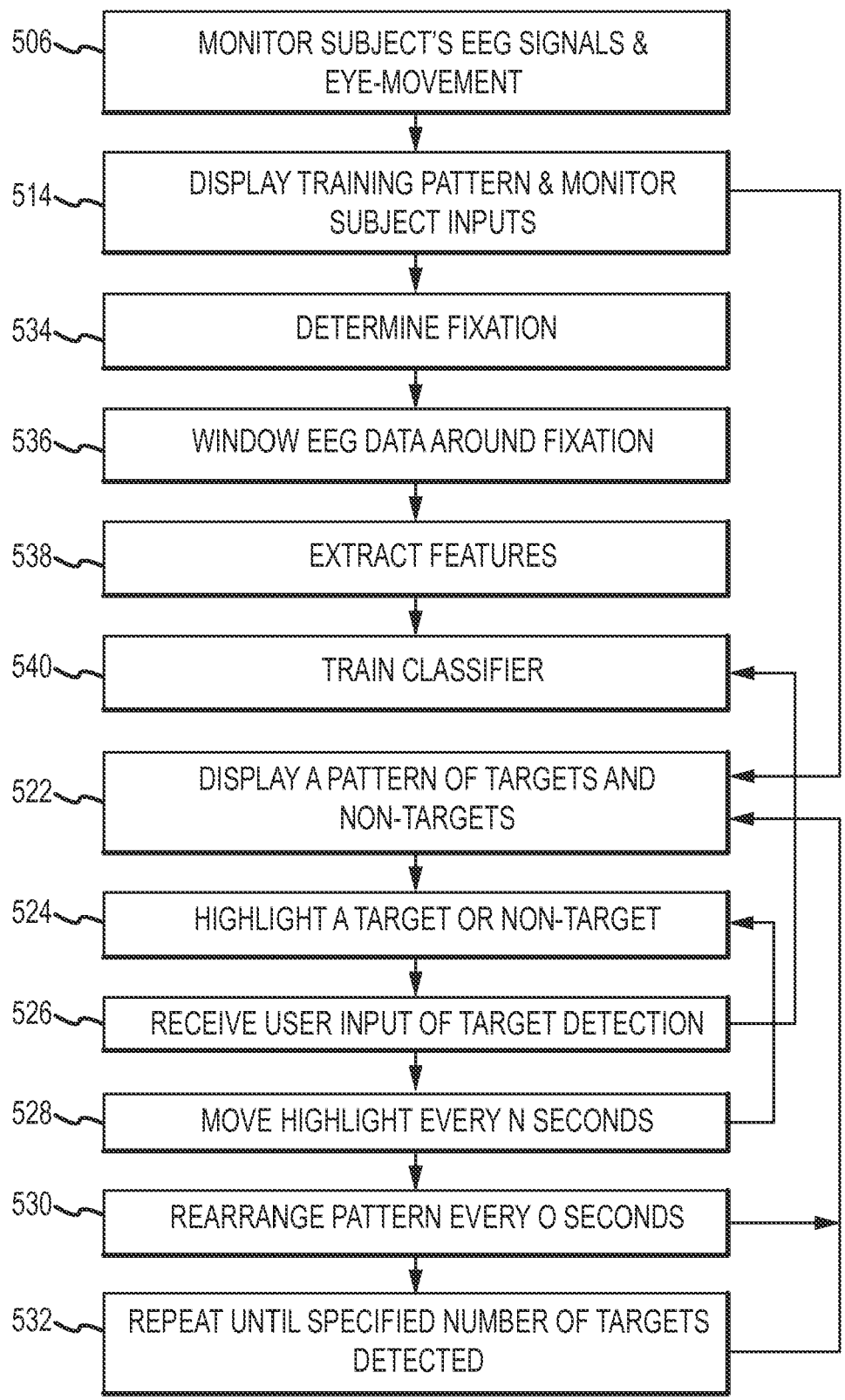

Referring now to FIGS. 10a and 10b, EEG electrodes 500 are attached to the scalp of a subject 502 and an eye tracker 504 is provided to monitor the subject's EEG signals and eye-movement during training (step 506). A training pattern 508 is displayed on display 510 and operator inputs via a keyboard 512 are monitored (step 514). The EEG signals, eye movement signals and operator input are provided to a computing device 516 (e.g. one or more processors and memory) that processes the data to train the classifier. In this embodiment, the classifier comprises a pre-fixation locked sub-classifier, a post-fixation locked sub-classifier and a fusion classifier as shown in FIG. 6b.

Computing device 516 displays pattern 508 including both targets 516 and non-targets 518 over a background 520 (step 522). In this embodiment, pattern comprises a spatially uniform array of letters (Ls and Ts) overlaid on a natural scene reminiscent of the expected imagery the subject will be confronted with during normal task performance. This array consists of only one T (target) and the remaining letters are Ls displayed in random orientations. Computing device 518 highlights one of the targets or non-targets (e.g. letters) for M milliseconds (e.g. 100-2000 ms) (step 524). In this embodiment, the computing device displays a red circle 525 centered on the letter. The subject is instructed to quickly saccade to the highlighted letter and press a button on the keyboard as soon as they determine there is a T inside the red circle (e.g. a highlighted target). Computing device 516 receives the operator input for target detection (step 526). The highlighting acts as a pre-fixation stimulus that causes the subject to saccade to the highlighted location. The act of detecting the target and pressing the button acts as a post-fixation stimulus.

The computing device moves the highlighted region to another target/non-target (letter) every N seconds (e.g. 0.5 to 3 seconds) (step 528) prompting the operator to press a button if a target is detected. The computing device re-arranges the pattern, typically randomly, every 0 seconds (5-20 seconds) (step 530) and steps 522, 524, 526 and 528 are repeated. The computing device repeats the procedure from step 522 to 530 until a specified number of targets (e.g. 30-40) have been detected (step 532).

While the pattern is being displayed to the subject and the subject is detecting targets, the computing device monitors the EEG signals, eye movement signals and operator inputs. For each highlighted area (letter), the computing device determines a fixation event (step 534). The computing device windows the EEG data around the fixation event (step 536). In this embodiment, the computing device separates the data into a pre-fixation window (e.g. −300 ms to 0 ms) and a post-fixation window (e.g. 0 ms to 700 ms). The computing device extracts features from the windowed EEG data (step 538). In this embodiment, the computing device extracts separate features from the pre and post-fixation locked windows. The features may or may not be the same. The computing device uses the extracted features and the knowledge of whether each fixation was based on a target or non-target to train the pre and post-fixation locked and fusion classifier (step 540). The pre-fixation locked sub-classifier learns the pattern of brain activity for responses during the pre-fixation window. The post-fixation locked sub-classifier learns both the pattern for early response due to detection during pr-fixation and the response due to target detection during post-fixation. The fusion classifier that combines input from both classifiers learns a general concept of target detection regardless of whether the stimulus if pre or post-fixation.

Figure 11:
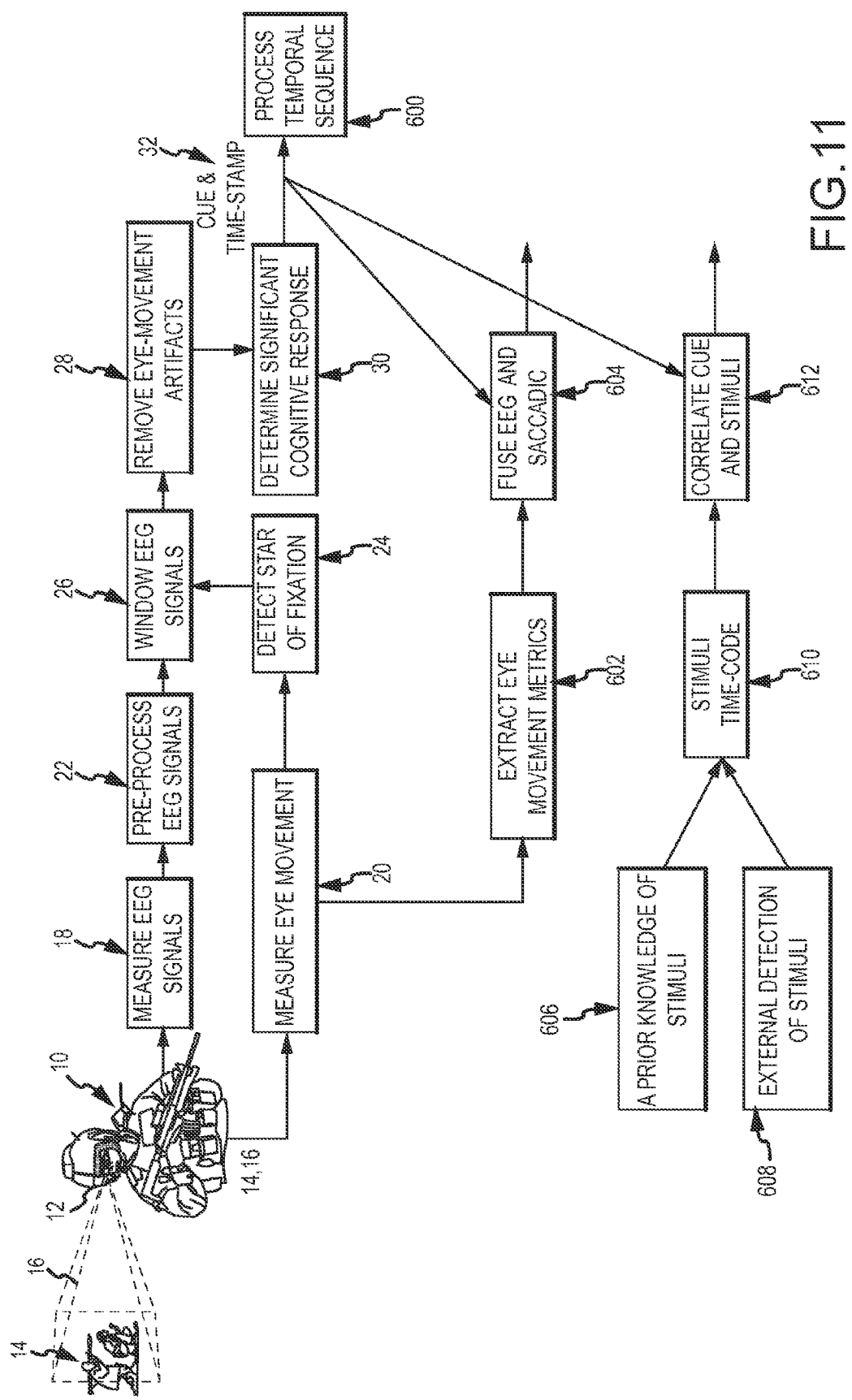
FIG. 11 is a block diagram of an alternate embodiment for fixation-locked measurements of brain responses to natural stimuli.

Referring now to FIG. 11, the fixation-locked measurement technique illustrated in FIG. 1 may be augmented with other sources of information or additional processing to enhance the detection of significant cognitive brain responses. These other sources may directly effect either the binary decision or likelihood of the cue. Alternately, these sources may augment the cue with additional information.

The temporal sequence of cues 32 may be processed (step 600) to enforce or reject the cue decision or likelihood. For example, if the stimulus represents a real threat the operator will tend to dwell on the stimulus and engage higher cognitive processes to respond to the threat. If a relevant stimulus is moving, the operator will tend to follow the stimulus in what is known as "smooth pursuit". Conversely, if the stimulus is a false alarm the cue will diminish rapidly and the operator will continue to scan in a more random manner.

The measurements of the free eye movement may be used to extract eye movement ("saccade") metrics (step 602) that may be fused (step 604) with the cues. Fusion may enforce or reject the cue decision or likelihood or may add the saccade metric as another part of the output. These saccade metrics may include where the operator is looking, the overall pattern of eye movement, duration of fixation, the length of the saccade, direction of the saccade and persistence of fixation in an approximate direction (e.g. a sequence of fixations all looking in approximately the same direction).

External knowledge of the stimuli, either a priori knowledge of the stimuli (step 606) such as might occur in the controlled presentation of language learning materials or external detection of stimuli (step 608) such as might be provided by acoustic or imaging sensors, can be used to provide a stimuli time-code (step 610). This time-code can be correlated to the fixation-event time code (step 612). This allows external knowledge of the stimulus to be correlated to and processed with the cues. For example, in language learning the system may be able to correlate a specific query to a specific cue. In an urban combat environment, command and control may be able to correlate a sensed condition(imaging, acoustic or other) to a specific cue.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A method of single-trial detection of significant cognitive responses to stimuli, comprising:
   measuring EEG data of an operator's brain activity to stimuli from a plurality of electrodes placed on the operator's scalp;
   tracking the operator's free eye movement to determine fixation events;
   applying a fixation-locked window to the EEG data to generate a time segment of EEG data for each said fixation event;
   extracting one or more features from each time segment of EEG data;
   for each said fixation event, presenting said one or more features to a classifier to generate a fixation-locked cue as a likelihood output indicative of whether the operator exhibited a significant cognitive response to a presented stimulus; and
   outputting a sequence of the cues with a time code of the associated fixation event.

2. The method of claim 1, wherein the cues and time-code are output in real time.

3. A method of single-trial detection of significant cognitive responses to stimuli, comprising:
   measuring EEG data of an operator's brain activity to stimuli from a plurality of electrodes placed on the operator's scalp;
   tracking the operator's free eye movement to determine fixation events;
   applying a fixation-locked window to the EEG data to generate a time segment of EEG data for each said fixation event, wherein the fixation-locked window comprises a pre-fixation window including EEG data before the fixation event and a post-fixation window including EEG data after the fixation event;
   extracting one or more features from each time segment of EEG data;
   for each said fixation event, presenting said one or more features to a classifier to generate a fixation-locked cue indicative of whether the operator exhibited a significant cognitive response to a presented stimulus; and
   outputting a sequence of the cues with a time code of the associated fixation event.

4. The method of claim 3, wherein the cue is a binary decision output.

5. The method of claim 3, wherein the cue is a likelihood output.

6. The method of claim 3, wherein said one or more features are extracted separately from the EEG data in said pre-fixation and post-fixation windows.

7. The method of claim 6, wherein the features extracted from the EEG data in the pre-fixation window are presented to a pre-fixation locked sub-classifier that generates a pre-fixation cue, the features extracted from the EEG data in the post-fixation window are presented to a post-fixation locked sub-classifier that generates a post-fixation cue and the pre-fixation cue and post-fixation cue are presented to a fusion classifier that generates the cue.

8. The method of claim 7, wherein the sub-classifiers are trained by:
   monitoring a subject's EEG signals and eye-movement;
   displaying a pattern of targets and non-targets to the subject as stimuli;

highlighting in sequence a different one of the targets or non-targets causing the subject's eyes to saccade to the highlighted target or non-target;

monitoring subject input indicating subject detection of a highlighted target;

processing the subject's eye-movement to determine a fixation-event for each highlighted target or non-target;

applying a pre-fixation window and a post-fixation window to the EEG data to generate pre-fixation and post-fixation time segments of EEG data fox each said fixation event;

separately extracting one or more pre-fixation and one or more post-fixation features from said pre-fixation and post-fixation time segments of EEG data, respectively; and for each said fixation event, presenting said one or more pre-fixation features and a target/non-target supervised output to train the pre-fixation sub-classifier to generate a pre-fixation cue indicative of whether the subject exhibited a significant cognitive response, presenting said one or more post-fixation features and a target/non-target supervised output to train the post-fixation sub-classifier to generate a post-fixation cue indicative of whether the subject exhibited a significant cognitive response and presenting the pre-fixation and post-fixation cues and the target/non-target supervised output to train a fusion classifier to generate a fixation-locked cue indicative of whether the subject exhibited a significant cognitive response.

9. The method of claim 7, wherein said step of extracting features from the EEG data in the post-fixation window and presenting them to the post-fixation locked sub-classifier comprises:

subdividing the time segment EEG data in the post-fixation window into a plurality of time sub-segments each with a different offset to the fixation-event;

separately extracting features from each said time sub-segment of EEG data;

presenting the extracted features to a respective plurality of spatial sub-classifiers trained to detect spatial patterns of said extracted features during different time segments after the fixation event and to generate first level outputs indicative of the occurrence or absence of a significant brain response; and combining the plurality of spatial sub-classifier first level outputs to detect temporal patterns across the different time sub-segments relating to the evolution of the non-stationary brain response to task-relevant stimulus and to generate a second level output as the post-fixation cue indicative of the occurrence or absence of the significant non-stationary brain response.

10. The method of claim 9, wherein the first level outputs are combined using a feature-level fuser implemented using a probabilistic or recurrent learning method.

11. The method of claim 9, wherein the first level outputs are maximum likelihood estimates that are combined using a decision-level fuser to achieve an optimal combination of the maximum likelihood estimates achievable.

12. The method of claim 9, wherein said step of extracting features from the EEG data in the pre-fixation window and presenting the features to the pre-fixation locked sub-classifier comprises:

subdividing the time segment EEG data in the pre-fixation window into a plurality of time sub-segments each with a different offset to the fixation-event;

separately extracting features from each said time sub-segment of EEG data;

presenting the extracted features to a respective plurality of spatial sub-classifiers trained to detect spatial patterns of said extracted features during different time segments before the fixation event and to generate first level outputs indicative of the occurrence or absence of a significant brain response; and combining the plurality of spatial sub-classifier first level outputs to detect temporal patterns across the different time sub-segments relating to the evolution of the non-stationary brain response to task-relevant stimulus and to generate a second level output as the pre-fixation cue indicative of the occurrence or absence of the significant non-stationary brain response.

13. The method of claim 7, wherein the stimuli comprise both pre-fixation stimuli in which the stimulus precedes the fixation-event and post-fixation stimuli in which the stimulus and fixation-event coincide.

14. The method of claim 3, wherein the classifier generates a tag with each cue that classifies either the type of stimulus that triggered the response or the type of brain activity that triggered the response.

15. The method of claim 14, wherein the tag identifies a particular event related potential (ERP) that triggered the response.

16. The method of claim 3, further comprising:
processing the sequence of time-coded cues to reinforce or reject the cue.

17. The method of claim 3, further comprising:
computing a saccade metric from the free eye movement between fixation events.

18. The method of claim 3, wherein the presentation of stimuli to the operator is unconstrained in time and position with respect to the operator.

19. A method of single-trial detection of significant cognitive responses to stimuli, comprising:

measuring EEG data of an operator's brain activity to stimuli from a plurality of electrodes placed on the operator's scalp;

providing a time-code for the stimuli;

tracking the operator's free eye movement to determine fixation events;

applying a fixation-locked window to the EEG data to generate a time segment of EEG data for each said fixation event;

extracting one or more features from each time segment of EEG data;

for each said fixation event, presenting said one or more features to a classifier to generate a fixation-locked cue indicative of whether the operator exhibited a significant cognitive response to a presented stimulus;

outputting a sequence of the cues with a time code of the associated fixation event; and correlating the time-code of the output cues with the time code of the stimuli.

20. An apparatus for single-trial detection of significant cognitive responses to stimuli, comprising:

a plurality of electrodes configured to be placed on the operator's scalp that measure EEG data of the operator's brain activity to stimuli;

an eye-tracking device that tracks the operator's free eye movement and generates eye movement signals;

a fixation processor that processes the eye movement signals to generate time-code fixation events;

a signal processor that applies a pre-fixation window to generate a time segment of EEG data before the fixation event and a post-fixation window to generate a time segment of EEG data after the fixation event to the EEG data for each said fixation event; and a cognitive response processor comprising a feature extractor that extracts one or more features from the EEG data in each of the pre-fixation and post-fixation windows for each time segment of EEG data and presents said one or more features to pre-fixation and post-fixation locked classifiers, respectively, to generate pre-fixation and post-fixation cues that are presented to a fusion classifier to generate a sequence of fixation-locked time-coded cues indicative of whether the operator exhibited a significant cognitive response to a stimulus.

21. The apparatus of claim 20, further comprising:
a processor that computes a saccade metric from the free eye movement between fixation events.

22. An apparatus for single-trial detection of significant cognitive responses to stimuli, comprising:
a plurality of electrodes configured to be placed placed on the operator's scalp that measure EEG data of the operator's brain activity to stimuli;
an eye-tracking device that tracks the operator's free eye movement and generates eye movement signals;
a fixation processor that processes the eye movement signals to generate time-code fixation events;
a signal processor that applies a fixation-locked window to the EEG data to generate a time segment of EEG data for each said fixation event, wherein said signal processor subdivides the time segment EEG data into a plurality of time sub-segments each with a different offset to the fixation-event; and
a cognitive response processor comprising a feature extractor that extracts one or more features from each said time sub-segment of EEG data and presents the extracted features to a respective plurality of spatial sub-classifiers trained to detect spatial patterns of said extracted features during different time sub-segments and to generate first level outputs indicative of the occurrence or absence of a significant brain response, said plurality of first level outputs presented to a temporal classifier trained to detect temporal patterns across the different time sub-segments relating to the evolution of the non-stationary brain response to task-relevant stimulus and to generate a second level output as a sequence of fixation-locked time-coded cues indicative of the occurrence or absence of the significant non-stationary brain response to a stimulus.

23. A method of training a classifier for single-trial detection of significant cognitive responses to pre-fixation and post-fixation stimuli, comprising:

monitoring a subject's EEG signals and eye-movement;
displaying a pattern of targets and non-targets to the subject;
highlighting in sequence a different one of the targets or non-targets causing the subject's eyes to saccade to the highlighted target or non-target;
monitoring subject input indicating subject detection of a highlighted target;
processing the subject's eye-movement to determine a fixation-event for each highlighted target or non-target;
applying a fixation-locked window to the EEG data to generate a time segment of EEG data for each fixation-event;
extracting one or more features from said time segment of EEG data; and
for each said fixation event, presenting said one or more features and a target/non-target supervised output to train the classifier to generate a fixation-locked cue indicative of whether the subject exhibited a significant cognitive response to a target.

24. The method of claim 23, wherein said fixation-locked window comprises a pre-fixation window and a post-fixation window and said classifier comprises a pre-fixation locked sub-classifier, a post-fixation locked sub-classifier and a fusion classifier, the method further comprising:
separately extracting one or more pre-fixation and one or more post-fixation features from pre-fixation and post-fixation time segments of EEG data, respectively; and
for each said fixation event, presenting said one or more pre-fixation features and the target/non-target supervised output to train the pre-fixation sub-classifier to generate a pre-fixation cue indicative of whether the subject exhibited a significant cognitive response to targets, presenting said one or more post-fixation features and the target/non-target supervised output to train the post-fixation sub-classifier to generate a post-fixation cue indicative of whether the subject exhibited a significant cognitive response to targets and presenting the pre- and post-fixation cues and the target/non-target supervised output to train a fusion classifier to generate a fixation-locked cue indicative of whether the subjected exhibited a significant cognitive response to targets.

25. The method of claim 23, wherein the pattern of targets and non-targets is rearranged periodically.

26. The method of claim 23, wherein the pattern is displayed until a specified number of targets is detected.

27. The method of claim 23, wherein the pattern is displayed on background reminiscent of an expected background the subject will be confronted with during task performance.

* * * * *